United States Patent

Howarth et al.

[11] 4,132,712
[45] Jan. 2, 1979

[54] ANTIBACTERIAL AGENTS

[75] Inventors: Thomas T. Howarth, Ewhurst; Irene Stirling, Worcester Park; David F. Corbett, Reigate, all of England

[73] Assignee: Beecham Group Limited, England

[21] Appl. No.: 717,900

[22] Filed: Aug. 26, 1976

[30] Foreign Application Priority Data

Oct. 13, 1975 [GB] United Kingdom ............ 41889/75

[51] Int. Cl.² .................................... C07D 498/04
[52] U.S. Cl. ........................... 260/307 FA; 424/272
[58] Field of Search ............... 260/307 FA; 424/272

[56] References Cited
PUBLICATIONS

Golding et al., C.A. 83, 178893v (1975).

Primary Examiner—Raymond V. Rush
Attorney, Agent, or Firm—Jacobs & Jacobs

[57] ABSTRACT

Compounds of the formula

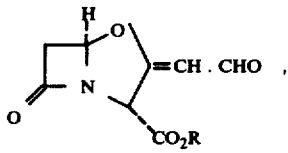

wherein $CO_2R$ is an ester group, are useful for their β-lactamase inhibitory activity.

4 Claims, No Drawings

ANTIBACTERIAL AGENTS

The present invention relates to β-lactam containing compounds, to their preparation and to compositions containing them.

Belgian Pat. No. 827926 discloses inter alia clavulanic acid and its salts and esters which substance clavulanic acid has the formula (I):

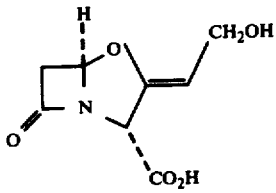

Clavulanic acid and its salts and esters are able to inhibit β-lactamases from a range of bacteria and owing to this useful property are able to enhance the effectiveness of penicillins and cephalosporins against many gram-positive and gram-negative bacteria. It has now been discovered that certain derivatives of clavulanic acid also possess useful β-lactamase inhibitory activity.

Accordingly the present invention provides the compounds of the formula (II):

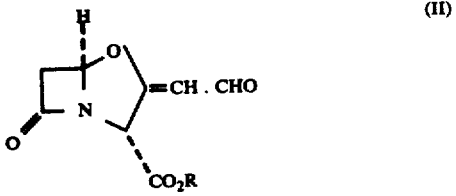

wherein $CO_2R$ is an ester group.

Suitably R is an inert group of up to 20 carbon atoms.

Most suitably R is a hydrocarbon group of up to 14 carbon atoms optionally substituted by halogen or by a group of the formula $OR^1$, $OCOR^1$, $SR^1$, $SOR^1$, $SO_2R^1$, $COR^1$ or $CO_2R^1$ wherein $R^1$ is a hydrocarbon group of up to 6 carbon atoms.

Favourably R is a hydrocarbon group of up to 4 carbon atoms optionally substituted by a group of the formula $OR^1$, $OCOR^1$, $SR^1$, $SOR^1$ or $SO_2R^1$ wherein $R^1$ is a hydrocarbon group of up to 6 carbon atoms.

Particularly suitable compounds of this invention include those of the formulae (III) and (IV):

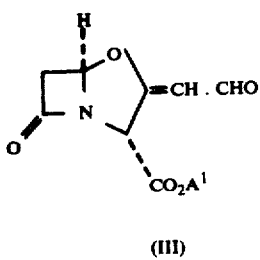

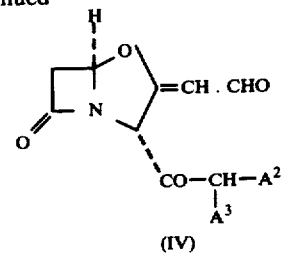

wherein $A^1$ is an alkyl group of up to 4 carbon atoms optionally substituted by halogen or by $OA^4$, $O.COA^4$ or $CO.A^4$ wherein $A^4$ is an alkyl group of up to 4 carbon atoms or a phenyl group; $A^2$ is a hydrogen atom or an alkyl group of up to 4 carbon atoms or a phenyl group optionally substituted by halogen or $A^5$ or $OA^5$ where $A^5$ is an alkyl group of up to 4 carbon atoms; and $A^3$ is a phenyl group optionally substituted by halogen or $A^6$ or $OA^6$ where $A^6$ is an alkyl group of up to 4 carbon atoms.

Preferred compounds of the formula (II) include methyl, ethyl, phenyl, benzyl, acetoxymethyl, pivaloyloxymethyl, phthalidyl, benzhydryl, methoxybenzyl, dimethoxybenzhydryl, allyl, acetonyl and the like esters.

Particularly prepared compounds of the formula (II) include the benzyl and benzhydryl esters.

The present invention also procides pharmaceutical compositions which comprise a compound of the formula (II) as hereinbefore described together with a pharmaceutically acceptable carrier.

Most suitably the compositions of this invention will contain from 50 mg to 1000 mg of the compound of formula (II).

If desired the composition of this invention may also comprise a penicillin or cephalosporin.

Suitable compositions will be similar to those described in Belgian Pat. No. 827926.

The present invention also provides a process for the preparation of the compounds of the formula (II) which process comprises the oxidation of the corresponding ester of clavulanic acid.

The oxidation reaction of the ester of clavulanic acid will take place under mild oxidising conditions that will convert the allylic hydroxyl group into an allylic aldehydic group without oxidising the double bond. The reaction will be carried out in an inert organic solvent at a non-extreme temperature.

Suitable inert organic solvents include conventional hydrocarbon, halogenated hydrocarbon or ether solvents.

The reaction may be best carried out at a temperature between −20° C. and +50° C., for example between 0° C. and 25° C. and most conveniently at an ambient temperature.

In one form the oxidation reaction of this invention comprises the ultra-violet irradiation of an ester of clavulanic acid in the presence of oxygen.

Suitable sources of radiation include medium pressure mercury vapour lamps and the like.

Suitably the solvent for this reaction is a hydrocarbon such as benzene, toluene or other conventional solvents used in photolytic reactions.

Suitably this reaction is carried out at an ambient or near ambient temperature, for example 10°–25° C.

Another form of the oxidation reaction of this invention comprises the reaction of an ester of clavulanic acid with an oxidising agent that oxidises an allylic hydroxyl group in preference to a double bond.

Oxidising agents that preferentially oxidise an allylic hydroxyl group are well known to those skilled in the chemical arts and include manganese dioxide, silver oxide and pyridinium chlorochromate.

Manganese dioxide is a convenient allylic oxidising agent. Pyridinium chlorochromate is a particularly convenient allylic oxidising agent.

Suitable solvents for this reaction include halogenated hydrocarbons such as dichloromethane.

Suitably the reaction is carried out at an approximately ambient temperature.

The compound of the formula (II) may be obtained from the reaction mixture by removal of the solvent present and isolation of the compound of the formula (II) from the resulting residue. Suitably the solvent will be removed under reduced pressure at a non-extreme temperature. The isolation of the compound of the formula (II) will be carried out by conventional methods, for example by chromatography.

The following Examples are illustrative of the invention.

EXAMPLE 1

Oxidation of Benzyl Clavulanate by photolysis

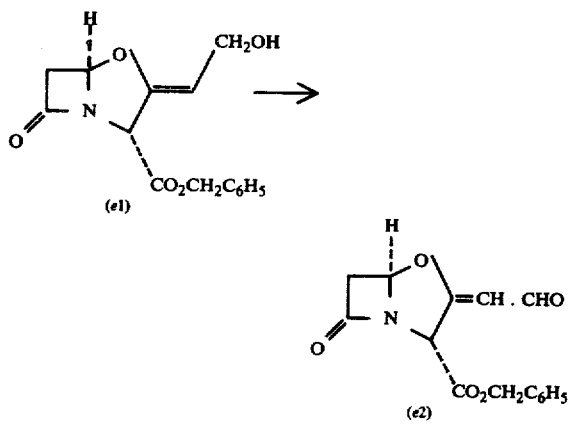

A solution of the benzyl ester of clavulanic acid (e1) in benzene was irradiated with a medium-pressure mercury lamp in a water-cooled 'quartz' jacket. The reaction was monitored by t.l.c. and h.l.p.c. and was shown to give two faster running components and one slower moving component. The solvent was removed and the residual oil fractionated on silica gel (elution with ethyl acetate and cyclohexane) and the slowest moving component on t.l.c. isolated. The i.r. spectrum of this material in methylene chloride showed absorption at 1810, 1750, 1675, 1645, 1600cm$^{-1}$ and the n.m.r. spectrum in CDCl$_3$ showed a signal characteristic of an aldehydic proton. On the basis of the spectral evidence structure (e2) was assigned to this compound.

EXAMPLE 2

Oxidation of Benzyl Clavulanate by Manganese Dioxide

The benzyl ester of a clavulanic acid (e1) (100 mg) was dissolved in dichloromethane (3 ml) and active manganese dioxide (1 g) was added. The reaction was left for 2 hours after which time t.l.c. showed reaction to have occurred. The reaction mixture was filtered and the filtrate evaporated under reduced pressure to give an oily residue which was chromatographed on silica gel (gradient elution with hexane and ethyl acetate) to yield the aldehyde (e2) (15 mg) as a colourless oil.

EXAMPLE 3

Oxidation of Benzyl Clavulanate by Pyridinium Chlorochromate

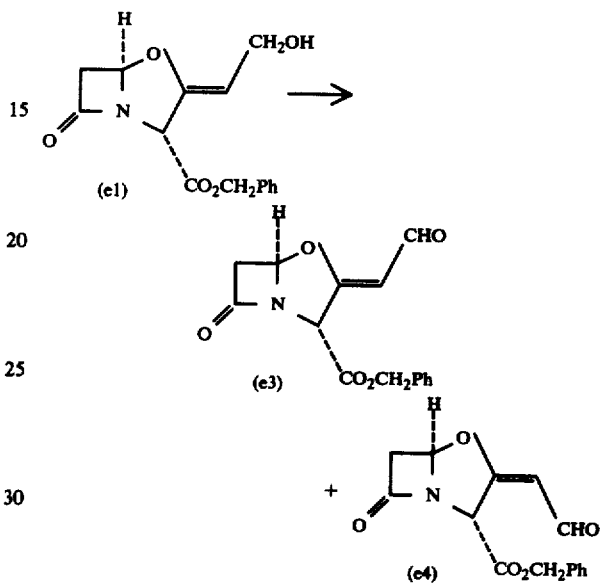

Benzyl clavulanate (e1) (0.75 g, 2.6 m mol) in CH$_2$Cl$_2$ (10 ml) was added in one portion to a suspension of pyridinium chlorochromate (1.0 g, 4.6 m mol) in CH$_2$Cl$_2$ (20 ml). After stirring at r.t. for 20 min. ether (50 ml) was added and the mixture filtered through Hiflo. The solvent was removed in vacuo and the product quickly chromatographed on silica gel using 50% petrol/EtOAc as eluant to afford a mixture of the (Z)-isomer (e3) and E-isomer (e4) of the aldehyde (ca. 1:1.2) (0.079 g, 10%); $\nu$ max. (CHCl$_3$) 1810, 1750, 1675 and 1650 cm$^{-1}$. p.m.r. (CDCl$_3$) (Z-isomer) 3.18 (1H, d, J 17 Hz, 6$\beta$-H), 3.59 (1H, dd, J 17, J$^1$ 3 Hz, 6$\alpha$-H), 5.15 (2H, s, CH$_2$O$_2$C), 5.24 (1H, d, J 1 Hz, 3-H), 5.33 (1H, dd, J 7.5, J$^1$ 1 Hz; =CH.CHO), 5.76 (1H, d, J 3 Hz, 5-H), 7.28 (5H, s, PhCH$_2$) and 9.81 (1H, d, J 7.5 Hz, CHO), (E-isomer) 3.11 (1H, d, J, 17 Hz, 6$\beta$-H), 3.55 (1H, dd, J 17, J$^1$ 3 Hz, 6$\alpha$-H), 5.15 (2H, s, CH$_2$O$_2$C), 5.65 (1H, d, J 1.5 Hz, 3-H), 5.82 (1H, dd, J 5., J$^1$ 1.5 Hz, : CH.CHO), 5.86 (1H, d, J 3 Hz, 5-H), 7.28 (5H, s, PhCH$_2$) and 9.52$\delta$ (1H, d, J 5 Hz, CHO). M$^+$ 287.079108 (C$_{15}$H$_{13}$NO$_5$ requires 287.079363; error 0.88 ppm).

EXAMPLE 4

Oxidation of Methyl Clavulanate by Pyridinium Chlorochromate

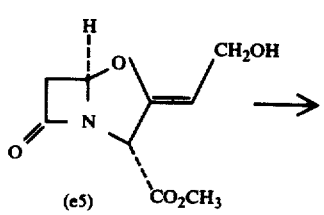

-continued

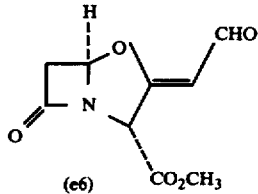

(e6)

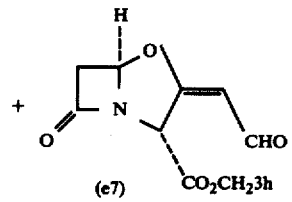

(e7)

Methyl clavulanate (e5) (0.95 g, 4.45 m mol) in $CH_2Cl_2$ (20 ml) was added to the pyridinium chlorochromate (3.0 g, 14 m mol) in $CH_2CH_2$ (20 ml). After stirring at r.t. for 20 min the reaction was worked-up as in Example 3 to afford a mixture of the aldehyde (e6) and aldehyde (e7) (ca. 1:1.5) (0.048 g, 5%); $\nu$ max. ($CHCl_3$) 1815, 1760, 1680 and 1650 cm$^{-1}$ p.m.r. ($CDCl_3$) (E-isomer) 3.13 (1H, d, J 17 Hz, 6$\beta$-H), 3.58 (1H, dd, J 17, J$^1$ 3 Hz, 6$\alpha$-H), 3.77 (3H, s, $CH_3O_2C$), 5.63 (1H d, J 1.5 Hz, 3-H), 5.86 (1H dd, J 5, J$^1$ 1.5 Hz, : CH.CHO), 5.90 (1H, d, J 3 Hz, 5-H), and 9.55 (1H, d, J 5 Hz, CHO), (Z-isomer) 3.21 (1H, d, J 17 Hz, 6$\beta$-H), 3.63 (1H, dd, J 17, J$^1$ 3 Hz, 6$\alpha$-H), 3.77 (3H, s, $CH_3O_2C$), 5.24 (1H, d, J 1 Hz, 3-H), 5.38 (1H, dd, J 7.5, J$^1$ 1 Hz, : CH.CHO), 5.79 (1H, d, J 3 Hz, 5-H) and 9.83$\delta$ (1H, d, J 7.5, CHO) M$^+$, 211 (molecular ion).

What we claim is:

1. A mixture of the E- and Z-isomers of a compound of the formula (II):

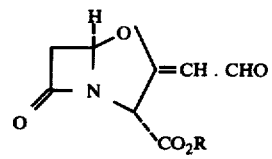

wherein $CO_2R$ is an ester group wherein R is methyl, ethyl, phenyl, benzyl, acetoxymethyl, pivaloyloxymethyl, phthalidyl, benzhydryl, methoxybenzyl, dimethoxybenzhydryl, allyl or acetonyl.

2. A mixture of the E- and Z-isomers of a compound of the formula (III) or (IV):

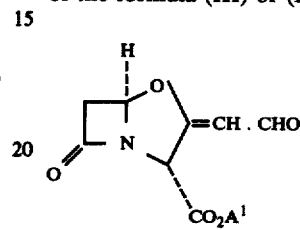

(III)

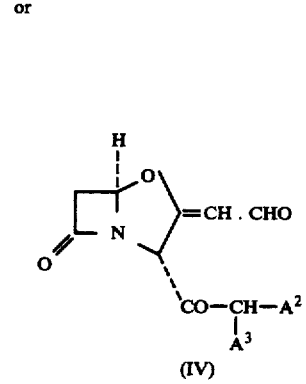

(IV)

wherein A$^1$ is alkyl of up to 4 carbon atoms unsubstituted or substituted by halogen or by a group of the formula OA$^4$, O.COA$^4$ or CO.A$^4$ wherein A$^4$ is alkyl of up to 4 carbon atoms or phenyl; A$^2$ is hydrogen, alkyl of up to 4 carbon atoms or phenyl unsubstituted or substituted by halogen or a group of the formula A$^5$ or OA$^5$ wherein A$^5$ is alkyl of up to 4 carbon atoms; and A$^3$ is phenyl unsubstituted or substituted by halogen or by a group of the formula A$^6$ or OA$^6$ wherein A$^6$ is alkyl of up to 4 carbon atoms.

3. A compound according to claim 1 wherein R is benzyl.

4. A compound according to claim 1 wherein R is methyl.